United States Patent [19]

Jones

[11] Patent Number: 4,783,470

[45] Date of Patent: Nov. 8, 1988

[54] HEMATIN DERIVED ANTICOAGULANT

[75] Inventor: Robert L. Jones, New York, N.Y.

[73] Assignee: The Rockefeller University, New York, N.Y.

[21] Appl. No.: 818,712

[22] Filed: Jan. 14, 1986

[51] Int. Cl.$^4$ .................... A61K 31/66; A61K 35/14
[52] U.S. Cl. .................................. 514/185; 514/822; 424/101; 540/145
[58] Field of Search ................ 424/101; 514/185, 822; 540/145

[56] References Cited

U.S. PATENT DOCUMENTS 4,098,780  7/1978  Lindroos ........................ 540/145

OTHER PUBLICATIONS

Green et al., Cited in Chem. Abstracts, vol. 99:192422c, 1983.

Primary Examiner—J. R. Brown
Assistant Examiner—Jacqueline M. Stone
Attorney, Agent, or Firm—Wyatt, Gerber Shoup, and Badie

[57] ABSTRACT

Anticoagulant is derived from hematin on standing in a slightly alkaline medium and may be isolated therefrom.

7 Claims, 8 Drawing Sheets

HEMATIN DERIVED ANTICOAGULANT

FIELD OF THE INVENTION

This invention relates to an anticoagulant derivable from hematin.

BACKGROUND OF THE INVENTION

Cardiovascular disease is the major cause of morbidity and mortality in our society. The broad category of cardiovascular disease refers to obstructive vascular disease and includes coronary artery disease, cerebral vascular insufficiency (stroke), peripheral vascular insufficiency and deep vein thrombosis. Although the precise pathogenesis of these diseases is unknown, each of these disorders is associated with activation of the blood clotting system and subsequent deposition of fibrin (clot) in the vascular space. This deposition either initiates or aggravates vascular obstruction and insufficiency. Thus the treatment of these diseases frequently involves some agent to interfere with blood coagulation.

Attempts to interact therapeutically with the blood clotting system focus on either increasing blood clot dissolution by the firbinolytic system or prevention of blood clot (fibrin) formation by an anticoagulant. The former approach has gained recent popularity with the production of specific fibrinolytic (plasminogen) activators by gene cloning technology. This includes production of tissue plasminogen activator, a potentially important fibrinolytic agent. These agents will actively dissolve preformed clots in the vascular space and thus will be used in acute vascular obstruction, e.g. acute myocardial infarction. Ths disadvantages of these agents are that they are applicable only in the acute phase of obstructive vascular disease and that they must be administered parenterally under close medical supervision.

Inhibition of blood coagulation for therapeutic purposes is currently attempted by one of two approaches: either the blood concentrations of certain clotting factors are lowered by vitamin-K antagonists such as warfarin, or the natural anticoagulant potential, namely antithrombin III heparin cofactor activity of the blood is increased by heparin. Recently, another approach involving specific synthetic or natural product inhibitors of the clotting proteases has been investigated. These inhibitors interact either reversibly or irreversibly with thrombin or other coagulation proteases to produce an anticoagulant effect.

Each of the anticoagulant agents which are currently in use or under investigation has advantages and disadvantages. Vitamin-K antagonists are orally effective and long acting but have a slow onset of action which is not easily reversed. There are also many problematic drug interactions which may be unrecognized by the clinician. Heparin, heparinoids and hirudin are rapid acting and very effective. Heparin is also easily reversed with protamine. However these agents are difficult to isolate and are only effective parentally due to their high molecular size and complex polysaccharide or polypeptide structure. The synthetic low molecular weight inhibitors appear to be effective orally and rapid acting. However, their effects are of short duration and may not be specific to the clotting proteases. Furthermore, the production costs of these synthetic compounds may be high.

Clearly there is room for improvement in the field of anticoagulants useful to treat those in need of such treatment.

THE INVENTION

An anticoagulant which is orally active, rapid acting and is derivable from hematin has now been discovered. It is referred to herein as HDA. The anticoagulant is further characterized by the following properties:
1. activity is inhibited by freshly prepared hematin.
2. activity is inhibited by tin protoporphyrin.
3. activity is inhibited by imidazole.
4. activity is inhibited by desferrioxamine
5. the inhibition by imidazole is reversed by ferric citrate.
6. activity is stable in the presence of ferrioxamine.
7. activity is stable in the presence of protoporphyrin IX.
8. active in presence of iron.

Before further describing this invention it may be helpful to provide a few definitions.

Hematin, also known as heme and as ferriprotoporphyrin IX is the nonprotein, insoluble iron porphyrin constituent of hemoglobin. It is $C_{34}H_{33}O_4N_4FeOH$.

Hemin, also known as Teichmann's crystals is the chloride of hematin. It is $C_{34}H_{32}N_4O_4FeCl$.

Tin protoporphyrin IX is ferriprotoporphyrin IX in which the iron has been replaced with tin Protoporphyrin IX is ferriportoporphyrin which is metal free.

For convenience this specification will be divided into a methods section, a conclusion section and a utility section. In the methods section, the various chemical, physical and biological procedures employed will be described in detail. In the conclusions sections, the conclusion with respect to the isolation, properties and biological activity of HDA based on the results observed with the defined methods will be described. In the utility section, the various procedures for usefully employing HDA will be described.

METHODS SECTION

Preparation of hematin and related solutions Hematin was prepared by two methods. 1) Hemin, assayed 101% purity by pyridine hemochromogen, (Porphyrin Products, Logan, Utah) was dissolved in 1N NaOH (0.2 ml for each ml of hematin solution) then 0.8 ml of potassium phosphate buffer (pH=7.5) was added. The final pH=7.5 was adjusted with 1N HCL. 2) Hemin was dissolved in 1N sodium carbonate (pH=12). The final pH of 7.5 was obtained by adding 1N HCL. Solutions of tin protoporphyrin IX, and protoporphyrin IX (Porphyrin Products, Logan, Utah) were prepared as per preparation 1) for hematin. The final concentration for all porphyrin solutions was 10 mg/ml. Hematin concentrations were confirmed by the pyridine hemochromogen assay, Friedman et al, *J. Biol. Chem.* 258:10564 (1983). Unless otherwise indicated, all other reagents were of the highest grade available from Sigma Chemicals Co., St. Louis, Mo., or Fisher Scientific Co., Pittsburgh, Pa.

Clotting Assays. Clotting times were measured using commercial reagents in duplicate with an automated optical coagulation recorder (Biodata Corp., Horsham, Pa.). They were also measured in the dark with a mechanical clot detection device (Fibrometer, Becton Dickinson). Prothrombin time (PT) and activated partial thromboplastin time (APTT) were measured with Simplastin, lot #4D831, and Automated PTT, lot #'s 4M610 and 4M842 (General Diagnostics, Morris Plains, N.J.). Thrombin time (TT) was measured with Bovine Topical Thrombin (Parke-Davis, Morris Plains, N.J.). Citrated (3.8%) normal plasma was obtained from normal healthy laboratory personnel and used fresh. Thrombin times were also performed with human fibrinogen (Kabi, Stokholn, Sweden) and purified human thrombin.

Ten microliter aliquots of porphyrin solutions were added to 1.0 ml plasma or fibrinogen solution (2.5 mg fibrinogen/ml phosphate buffer, pH=7.5) to make final concentrations of 0.01 to 0.10 mg hematin/ml. This range was chosen to approximate the range of plasma hematin concentrations seen in patients after intravenous hematin infusion. Unless otherwise indicated, anticoagulant activity (HDA) was assessed by the above clotting assays performed immediately after the addition of porphyrin solutions to normal plasma or fibrinogen solutions. Prolongation of clotting times was quantitated by comparing the results with clotting times from plasma which had not been treated with hematin solutions or to which buffer alone had been added.

In Vitro Generation Of HDA. Hematin and other porphyrin solutions were allowed to stand at 4° C. exposed to ambient light, exposed to constant incandescent light (40 watt lamp positioned 12 inches from the solution) or in total darkness. Hematin solutions were also aged in the presence of 2 mM of the antioxidants mannitol, sorbitol, 2-mercaptoethanol (2MCE), or butylated hydroxytoluene (BHT). Anticoagulant activity of porphyrin solutions was assessed periodically with plasma clotting assays as above for over six weeks of standing.

Anticoagulant activity (aged hematin) generated in vitro was tested in the presence of equimolar concentrations of fresh hematin, fresh and aged tin-protoporphyrin IX, fresh and aged protoporphyrin IX. It was also tested in the presence of varying concentrations of imidazole or desferrioxamine (Ciba Geigy), and in the presence of ferrioxamine, the iron chelate of desferrioxamine. Ferrioxamine was produced by mixing a molar excess of ferric chloride with desferrioxamine followed by alkalinization with NaOH to pH=8.0 to remove unbound ferric iron. Desferrioxamine or ferrioxamine were added before or after HDA was added to plasma.

Thin Layer Chromatography (TLC) of Aged Hematin. Hematin (aged 4 weeks) solution containing HDA was spotted on a pre-coated silica gel 60 plate (E. Merck, Darmstadt, Germany). A mixture of 2,6-lutidine and water (100 ml:60 ml) was placed in the bottom of a chromatographic tank (20×20×8 cm) and 3 small beakers containing 7N $NH_4OH$ were placed in the tank. After saturation of the tank with $NH_3$ vapor, the TLC plate was placed upright in the tank and ascending development was carried out for 3 hours. Plates were divided into bands, scraped and the resin extracted with 1N NaOH/95% ethanol. Extracts were dried in a Savant Speed-Vac concentrator to isolate the HDA. It was redissolved in equal volumes of phosphosaline buffer (pH=7.4), then tested for HDA by adding aliquots to plasma and performing APTT's.

High Performance Liquid Chromatography (HPLC) of Aged Hematin. Tetrabutylammonium hydroxide (TBAH) was purchased from Eastman-Kodak Co. Phosphate buffer was prepared using water purified to 18 MSL by a Milli-Q filtration system (Millipore Corp.). All solutions were deaerated by evacuation prior to use.

HPLC conditions included a series 3B solvent distributor (Perkin-Elmer Corp.), a $3\mu$ $C_{18}$ column (Perkin-Elmer, No.258-0160), a septumless syringe injector (Rheodyne 7105), and LC 75 spectrophotometer (Perkin-Elmer). The mobile phase solvent was methanol in 10 mM potassium phosphate buffer (pH 6.0) containing 5 mM TBAH. Methanol concentration was raised from 40% to 99.9% over 10 min. with a flow rate of 0.8 ml/min (13) Hematin was detected using absorption at 410 nm. Fractions were collected using a LKB Redi-Rac fraction collector. Data were analyzed by a 3600 Chromatography Data Station (Perkin-Elmer). Fractions were dried as for TLC, reconstituted in equal volumes of phosphosaline buffer, and then tested for HDA by adding 10 $\mu$l aliquots from each fraction to 1.0 ml plasma and performing TT's.

Dissociation of HDA from the parent hematin compound in plasma. Aged hematin with HDA was added to fresh normal citrated plasma (0.060 mg/ml) and incubated for 30 minutes. To assess total available HDA the incubated plasma was mixed with an equal volume of untreated plasma and a thrombin time performed. This time was compared with an untreated plasma thrombin time. HDA treated plasma was clotted with thrombin (5 units/ml) for 60 minutes, centrifuged at 2000×G for 30 minutes and the serum separated from the fibrin clot. The serum was then mixed with an equal volume of non-HDA treated plasma and a thrombin time performed. This was compared with the TT obtained with serum from non- treated plasma. Sera (treated and untreated) were also alkalinized with NaOH to pH=12, followed by addition of sodium dodecyl sulfate (0.5% final concentration) and then neutralized with HCL. Total HDA activity was then assessed with a TT for the dissolved clot (see below). This treatment did not significantly increase HDA releasable from serum samples. Plasma and serum hematin concentrations were assessed by measuring absorption at 405 or 610 nm and referring to a standard curve.

The clot from the HDA treated plasma was solubilized by alkalinization to pH 12 with NaOH and addition of sodium dodecyl sulfate (SDS) to a final concentration of 0.5%. The solubilized clot was neutralized to pH=7.5 with 1N HCL. The volume of the solubilized clot was adjusted with phosphosaline buffer (pH=7.4) to equal the volume of the plasma from which the clot was obtained. The fibrin clot solution was then tested for HDA by adding to an equal volume of normal plasma and peforming a TT as above. This result was compared with a TT performed with a clot solution from plasma which had not been treated with HDA. Neither treated nor untreated solubilized clots were clottable with thrombin.

Statistics. Results are expressed as mean and the range of observed values.

CONCLUSIONS SECTION

The Drawings. FIGS. 1 to 7 illustrate in graphic form the results of the certain of the studies described in the Methods Section.

The drawings will be better understood by reference to the following descriptions:

FIG. 1. Effect of light on generation of HDA in vitro. Hematin solutions (preparation #1, NaOH/Phosphate buffer and preparation #2, Carbonate buffer) were allowed to stand in the dark or exposed to incandescent light (40 Watt lamp at 12 inches) for 30 days. HDA was assessed at intervals by adding 10 $\mu$l aliquots (equivalent of 0.060 mg from fresh hematin solution) to fresh normal plasma and performing clotting assays. HDA units represent the percent above the control clotting times. Each point represents the mean and one standard deviation of three preparations.

FIG. 2. Effect of antioxidants on the generation of HDA in vitro. Hematin solutions were allowed to stand at 4° C. in the presence of 2 mM concentrations of mannitol sorbitol, 2-MCE or BHT. The solid line represents hematin allowed to stand without antioxidants. (A) Hematin solutions aged in the dark and (B) hematin solutions aged exposed to incadescent light.

FIG. 3. HDA in aged hematin solutions. Aged hematin solutions show a dose dependent prolongation of APTT when added to normal citrated plasma. Activity is expressed as a percentage over control APTT. Open circles represent actual hematin concentration measured in the aged hematin solution by absorption at 405 and 610 nm, Open boxes represent hematin concentration predicted from the concentration in solution when it was fresh. Closed circles show the activity in a fresh (non-aged) solution.

FIG. 5. Inhibition of HDA by Imidazole. Imidazole was added to fibrinogen or thrombin solutions prior to addition of HDA. Thrombin times were performed by adding treated thrombin to untreated fibrinogen (a) or by adding untreated thrombin to treated fibrinogen solution (b). Imidazole in concentrations of 10 to 50 mM significantly inhibits HDA. Addition of ferric citrate (50 mM) to the treated solutions reverses the inhibition of HDA produced by imidazole.

FIG. 6. Thin Layer Chromatography of aged hematin solution. Aged hematin solution was eluted on silica gel-60 with 2,6-lutidine and water in a tank saturated with $NH_3$ vapor. The plates were divided into bands which were scraped and the resin extracted for HDA. HDA was tested by adding aliquots from concentrated extracts to plasma and performing APTT's. The parent compound (hematin) elutes at RF 0.5. The major band of HDA elutes at a lower RF and is not associated with pigment.

FIG. 7. HPLC of fresh and aged hematin solutions. Hematin solutions were chromatogrammed on reverse phase ($c_{18}$) columns. HDA was tested by adding aliquots from each fraction to plasma and performing APTT's. HDA elutes significantly after the major band associated with fresh hematin solution. HDA also elutes in fractions not associated with absorption at 410 nm.

Figure 1:
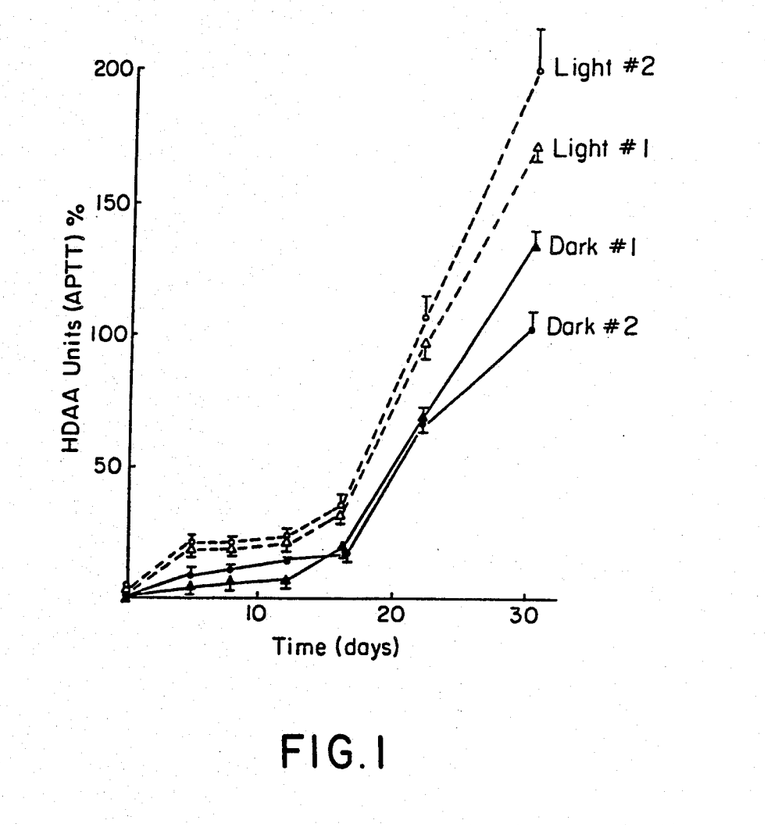

Generation of HDA in vitro. HDA was assessed at intervals in hematin solutions which were allowed to stand at 4° C. for over 6 weks in ambient light, direct incandescent light, or total darkness. The results of generation of HDA by the "aging" of hematin solutions in ambient light are seen in Table 1. The mean and range of values expressed as percent over control clotting times are shown for aging in ambient light for both preparation one (potassium phosphate buffer) and preparation two (carbonate buffer). Neither hematin preparation shows any anticoagulant activity (HDA) on day zero. However by day 50 both preparations have developed sufficient HDA activity to prolong clotting times by up to 188% (APTT) over control when added to a concentration of 0.060 mg hematin/ml plasma. Prolongation of clotting times was more pronounced with TT and APTT. FIG. 1 shows the dose dependent prolongation of clotting times (APTT) when aged or fresh hematin is added to normal plasma. In the aged preparaion, the amount of hematin added to plasma is expressed both as that measured by pyridine hemochromogen in the aged hematin solution and as the amount predicted from the original hematin concentration when made up fresh. The shift to the left of the actual amount relative to the predicted amount indicates a fall in hematin concentration in the aged solution compared to when it was fresh.

TABLE 1

HDA Generation from Hematin in vitro - "Aging" of Hematin
HDA UNITS + SD

| AGE OF SOLUTION (DAYS) | PREPARATION 1 | | | PREPARATION 2 | | |
|---|---|---|---|---|---|---|
| | PT | TT | APTT | PT | TT | APTT |
| 0 | 4.7 ±0.8 | 13.3 ±3.0 | 9.5 ±1.5 | 0.99 ±0.01 | 5.9 ±4.3 | 6.4 ±2.1 |
| 4 | 0.88 ±0.02 | 7.0 ±3.6 | 5.5 ±3.5 | 0.88 ±0.00 | 5.2 ±2.3 | 6.4 ±3.1 |
| 8 | 2.8 ±2.9 | 17.7 ±1.9 | 21.4 ±10.1 | 0.93 ±0.01 | 8.8 ±2.9 | 14.1 ±2.1 |
| 12 | 2.6 ±2.5 | 14.3 ±2.9 | 18.2 ±9.1 | 0.99 ±0.01 | 10.6 ±2.3 | 13.4 ±1.7 |
| 16 | 11.3 ±2.0 | 18.8 ±3.4 | 30.0 ±6.8 | 4.9 ±2.6 | 12.1 ±2.9 | 25.5 ±8.0 |
| 22 | 22.0 ±4.5 | 116.8 ±6.2 | 71.6 ±5.8 | 10.5 ±2.2 | 53.9 ±14.4 | 71.7 ±12.6 |
| 30 | 27.0 ±5.5 | 140.6 ±14.7 | 136.9 ±11.9 | 18.3 ±7.8 | 116.5 ±16.8 | 113.3 ±15.7 |
| 50 | 36.5 ±3.0 | 154.8 ±25.7 | 188.0 ±19.2 | 34.4 ±5.9 | 137.4 ±9.5 | 183.0 ±14.5 |

Figure 2A:
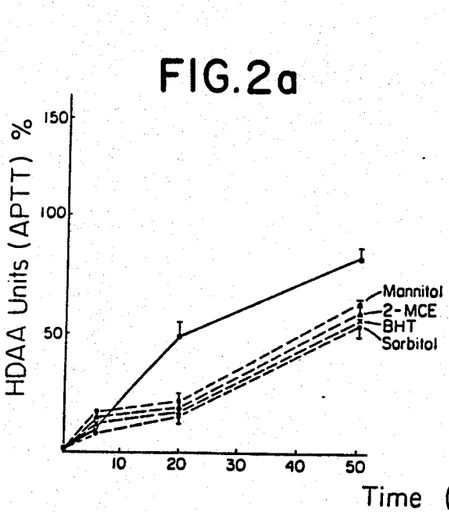
Figure 2B:
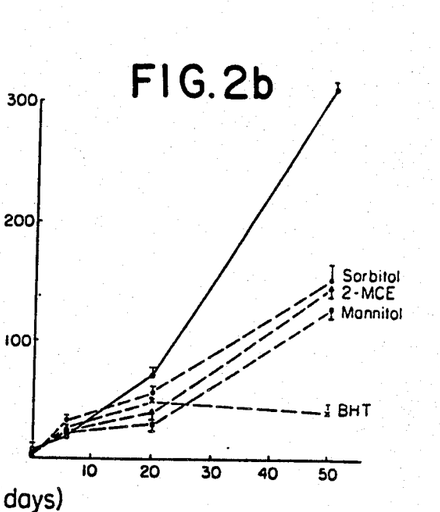

Acceleration and Retardation of HDA generation. FIG. 2 shows the results of aging hematin solutions in direct incandescent light or in total darkness. FIG. 2a shows that HDA generation in direct light is greater than that seen with ambient light. FIG. 2b shows that aging of hematin in total darkness generates lower levels of HDA activity.

While the presence or absence of light had an effect on the generation of anticoagulant activity in aging hematin solutions, clotting times performed with added aged hematin were equally prolonged when performed in the light or in the dark. Thus HDA activity (prolongation of clotting times) found in aged hematin solutions was not affected whether the clotting assays were performed in the absence or presence of light.

FIG. 2 also shows the results of HDA generation in the presence of various antioxidant compounds. At the concentrations used, none of the antioxidants had a significant effect on clotting times when added to normal plasma without hematin solutions present. When hematin solutions were aged in the presence of these antioxidants, significant retardation of the development of HDA was observed. Retardation of HDA generation by these compounds was seen in solutions aged both in the light (FIG. 2a) or in the dark (FIG. 2b) Supression of the generation of HDA was greatest in the solution aged in the light.

The results illustrated in FIGS. 1 and 2 show that HDA is derived from hematin by maintaining the solution at ambient temperatures, i.e. 25° to 45° C. in a slightly alkaline medium, e.g., pH 7.3 to 7.8. The generation is time dependent and accelerated by light. The acceleration by light suggests that an oxidation or free radical mediated alteration of hematin is responsible for the production of HDA. This suggestion is reinforced by the fact that antioxidants such as mannitol, sorbitol, 2-MCE and BHT retard the production of HDA.

Figure 3:
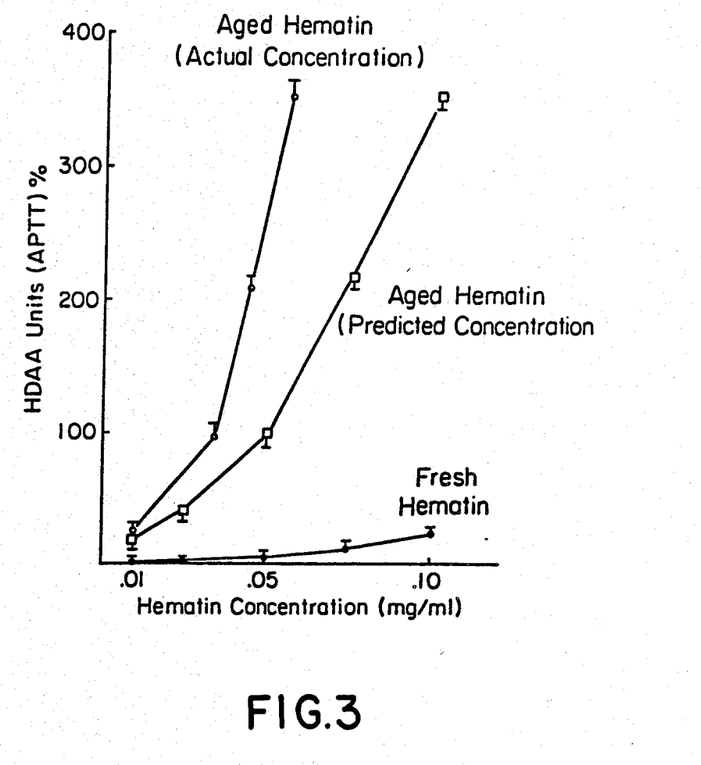
Figure 4:
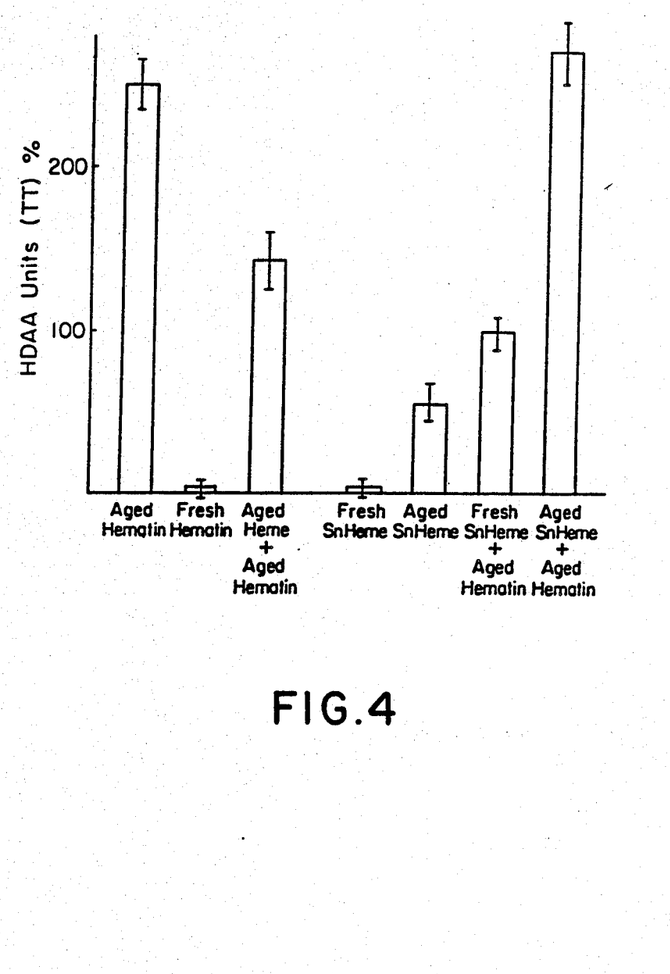
FIG. 4. Inhibitory Effect of fresh hematin and tin protoporphyrin IX on HDA. HDA was tested in the presence of equimolar amounts of fresh hematin, fresh or aged tin-protoporphyrin IX solutions by thrombin times. These solutions were also tested for anticoagulant activity withouth added aged heme (HDA). Equimolar concentrations of fresh hematin or tin-protoporphyrin IX significantly reduce HDA. Aged tin-protoporphyrin IX solution alone produces a significant prolongation of thrombin times. Addition of aged tin-protoporphyrin IX to aged hematin augments HDA.

Dissociation and separation of HDA from hematin in aged hematin solutions. HDA was dissociated from the parent hematin compound by TLC and HPLC. FIG. 3 shows that the major band of HDA activity (prolongation of APTT) elutes at an appreciably lower Rf than hematin in TLC. It is notable that the band with the highest activity is not associated with pigment. FIG. 4 shown the results of HPLC of fresh and aged hematin solutions. The elution pattern of absorption at 410 nm of fresh hematin solution clearly differs from that of aged hematin. HDA activity (prolongation of TT) elutes after the parent hematin peak in fractions with low absorption at 410 nm.

TLC and HPLC permit the isolation of HDA and clearly demonstrate a distinction between hematin and HDA. The results of the TLC and HPLC studies also suggest that HDA is a single derivative or degradation product of the in vitro hematin aging process.

Dissociation and separation of HDA from hematin in plasma. Normal citrated plasma with added aged hematin solution (0.06 mg/ml) was clotted with thrombin (5 units/ml) for 60 minutes at 37° C., centrifuged and the serum and fibrin clot separated. HDA was tested in both the serum and dissolved fibrin clot fractions by adding the fractions to an equal volume of normal plasma and performing thrombin times. The results are seen in Table 2. When compared to the corresponding control serum or dissolved clot fraction (not treated with HDA) the dissolved clot fraction prolonged the thrombin time considerably longer than the serum fraction (97% over control vs. 27.6% over control). This shows that HDA preferentially segregated into the clot fraction indicating that HDA may preferentially bind the fibrinogen. On the other hand, hematin as measured by absorption at 610 nm was largely distributed in the serum fraction.

TABLE II

SEGREGATION OF HDA AND HEMATIN INTO SERUM OR DISSOLVED CLOT FRACTIONS OF PLASMA

| | Whole Plasma | Dissolved Clot | Serum Fraction |
|---|---|---|---|
| HDA (% over) | 80.5 ±8.2% | 97.0 ±8.9% | 27.6 ±5.6% |
| Control TT | | | |
| Hematin Concentration(mg.) | .064 | .012± | .050± |
| (% added) | (100%) | (19.4 ± 10.2%) | (78.3 ± 5.8%) |

Figure 5A:
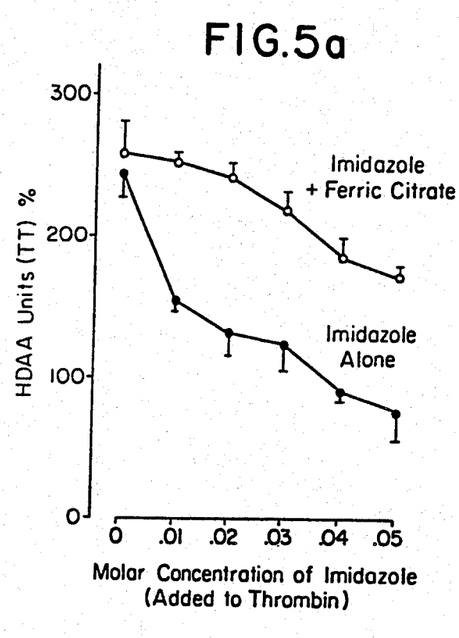
Figure 5B:
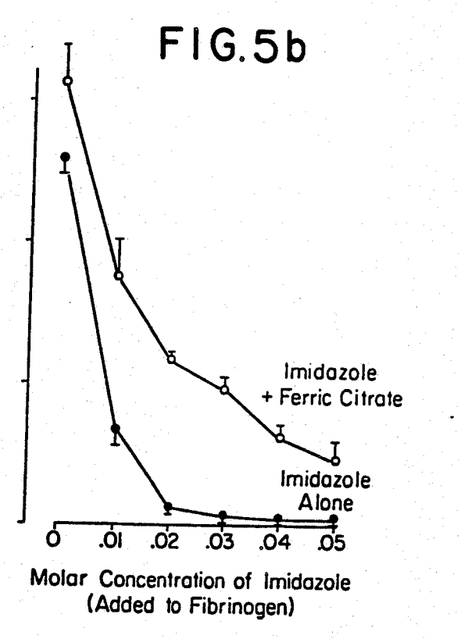

Inhibitors of HDA prolongation of clotting times. Prolongation of clotting times (HDA) found in aged hematin solutions was tested in plasma in the presence of fresh (nonaged) hematin solution, fresh or aged Sn-protoporphyrin IX or fresh or aged protoporphyrin IX. The results of the clotting times expressed as percent over control from these experiments are seen in FIG. 5. Neither fresh hematin nor fresh Sn-protoporphyrin IX alone had any significant effect, whereas aged Sn-protoporphyrin IX alone showed a small prolongation of thrombin times. When fresh hematin or fresh Sn-protoporphyrin IX were added in equimolar amounts with aged hematin, there was a significant reduction in HDA activity as measured by plasma thrombin times. Aged Sn-protoporphyrin IX added to plasma with aged hematin showed a small augmentation of HDA. It was also separately observed that neither fresh nor aged protoporphyrin IX had an effect on plasma clotting times when added alone or with equimolar concentrations of aged hematin.

The foregoing studies provide further evidence that HDA is a derivative of hematin rather than the parent compound. It is apparent that a breakdown product will bear some structural similarity to the parent compound. Therefore, the observed inhibition of anti-coagulant activity suggests that non-degraded metalloporphyrins such as tin protoporphyrin interact with or block specific sites on coagulation proteins which must be available for HDA activity. Also, neither fresh nor aged protoporphyrin IX, which is metal free, showed inhibition of HDA when added in equimolar amounts. The lack of anticoagulant activity or inhibition of anticoagulant activity produced by this compound, whether aged or fresh, indicates that a metal must be present in the porphyrin ring to cause breakdown to HDA or inhibition of HDA by the fresh porphyrin.

HDA was tested in the presence of varying concentrations of imidazole. Dose dependent reduction of HDA was seen when plasma clotting times were performed with the addition of imidazole (0-50 mM final concentration) prior to adding HDA. Imidazole was also added to either a purified fibrinogen or a purified thrombin solution five minutes prior to addition of HDA. Clotting times were performed by adding treated thrombin to untreated fibronogen or untreated thrombin to treated fibrinogen. In a purified fibrinogen and thrombin system, thrombin time prolongation produced by HDA was inhibited if imidazole was added first either to the fibrinogen or the thrombin, FIG. 6. Control experiments showed no effects on thrombin times when imidazole was added to either the thrombin or the fibrinogen solutions in the absence of HDA.

Figure 6:
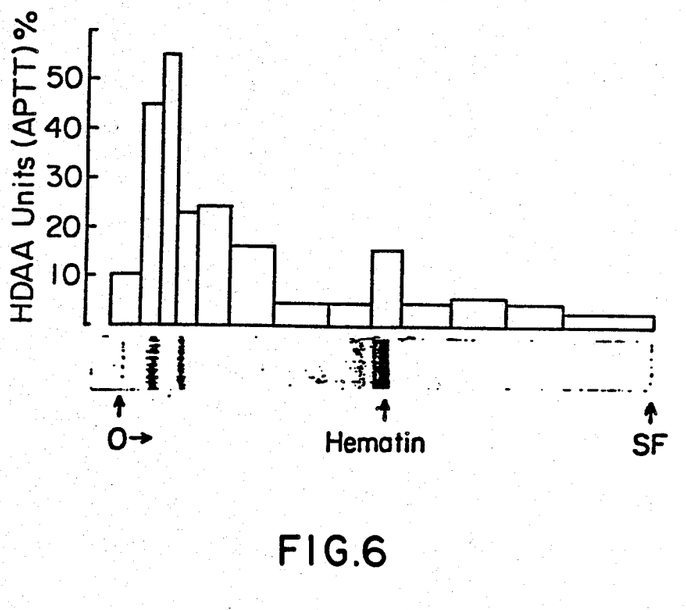

It will be clear from FIG. 6 that imidazole shows a dose dependent inhibition of HDA. More specifically, imidazole prevents or retards the inactivation of thrombin or fibrinogen. It also appears from FIG. 6 that this effect is more pronounced with fibrinogen. In the hemoglobin molecule, heme is known to bind to globin partially through an interaction of the iron of heme and a histidine residue (imidazole) of globin. Inhibition of HDA by imidazole and the observed reversal of this inhibition by iron as described in the following paragraph and shown in FIG. 6, suggests that iron or a metal atom play an important role in the action of HDA.

Since iron chelation by imidazole may participate in the inhibition of HDA, these experiments were also performed in the presence of 50 mM ferric citrate. Ferric citrate alone (no imidazole) produced no additional prolongation of clotting times beyond that produced by HDA. FIG. 6 shows that ferric iron as ferric citrate reverses the inhibition of HDA produced by imidazole.

Figure 7:
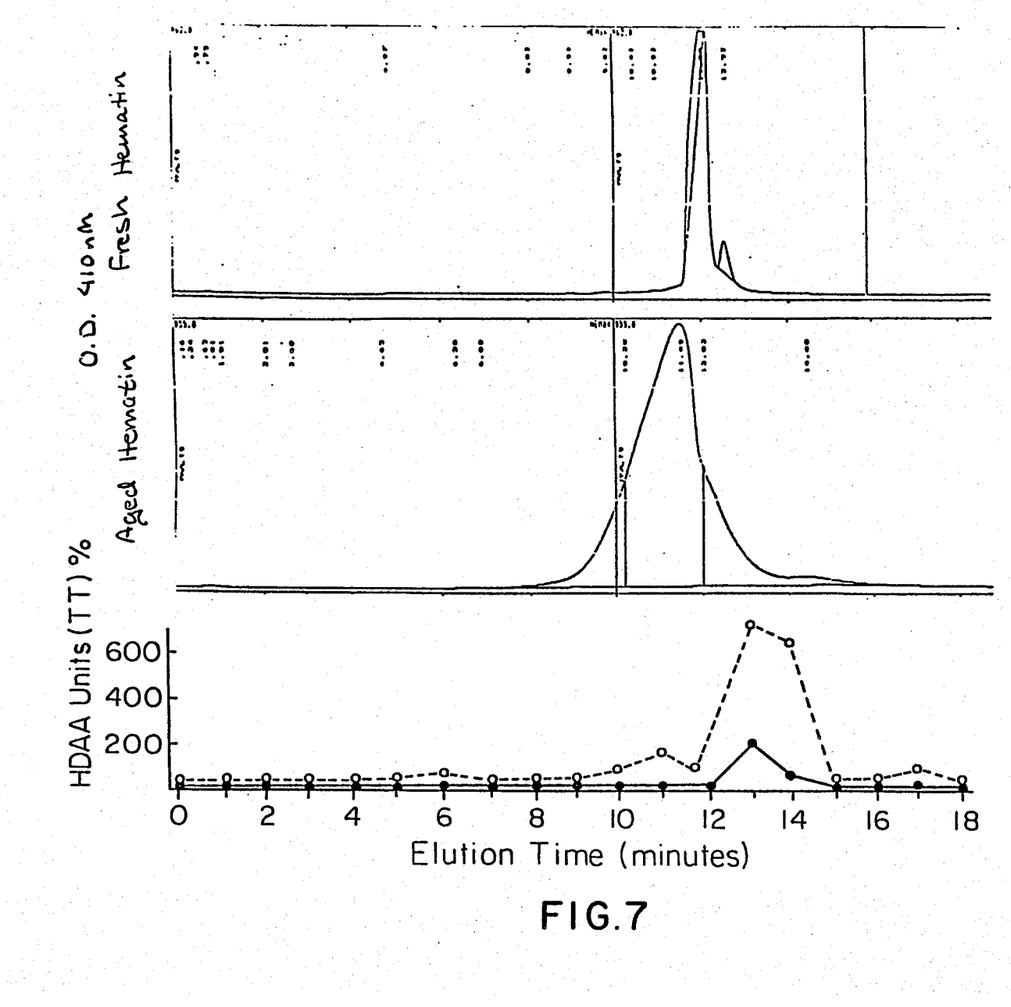
Figure 8:
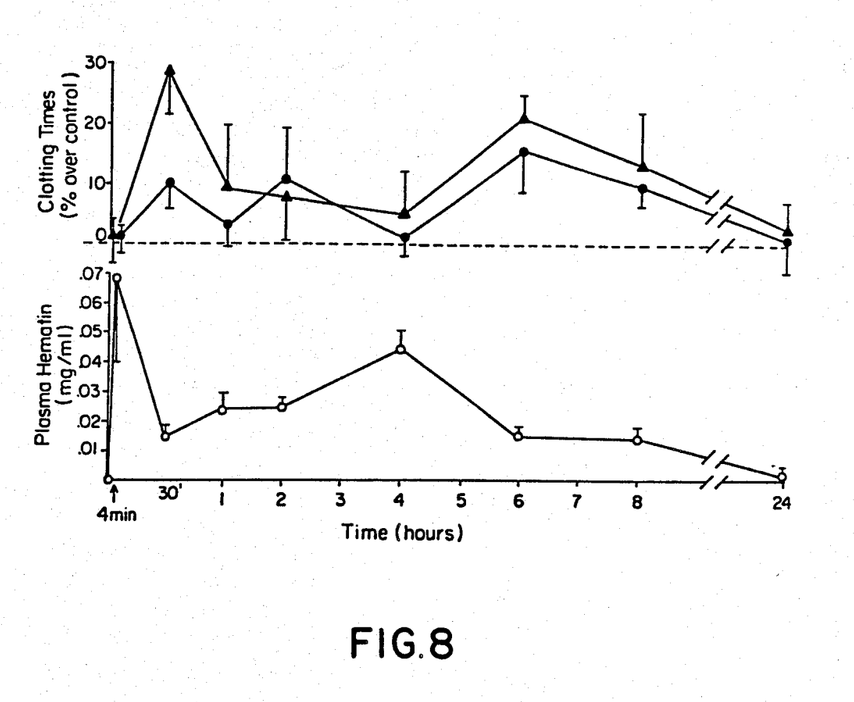

To further elucidate the role of iron in the mechanism of HDA activity, HDA was tested before (blockade) and after (reversal) the addition of the specific iron chelator. desferrioxamine. FIG. 7 shows the dose dependent (0–0.3 mg/ml) blockade of anticoagulant activity produced by desferrioxamine when added before HDA in purified fibrinogen/thrombin time experiment. This figure also shows that ferrioxamine, the iron chelate of desferrioxamine, produced no blockade of HDA activity.

Blockade and reversal of HDA by desferrioxamine is further evidence that iron is involved in the mechanism of HDA activity. Failure of ferrioxamine (the iron chelate of desferrioxamine) to inhibit HDA shows that the iron binding capacity of desferrioxamine is necessary for the inhibition.

Oral Activity. The oral bioavailability of HDA was established by studies in rats. In the study, five rats (300–350 gm male) received an oral preparation of degraded hematin by esophogeal-gastric cannula after an overnight fast. The hematin preparations were degraded for various lengths of time and varied in their anticoagulant activity. Following a 60 minute baseline period each rat received 1.0 ml of a degraded hematin solution (original concentration of hematin, 10 mg/ml) followed by a repeat dose 60 minutes later. Other, control rats, were similarly treated except that received either an equal volume of carbonate buffer or non-degraded (fresh) heparin.

Blood was sampled serially every 20 minutes through a catheter in the carotid artery. The catheter was kept open with a saline infusion maintained by a Harvard pump. At each time point, 400 $\mu$l of blood were drawn into 45 $\mu$l of 3.8% citrate anticoagulant. Duplicate APTT's were determined on the resultant plasma at each time point.

It was observed that, although there was a variation in the onset and degree of prolongation of APTT as a result of the administration of HDA, each rat showed a definite prolongation of APTT. No prolongation of clotting times was observed after the administration of the carbonate buffer or the fresh hematin.

It was further observed that there was no significant change in the color of the plasma during the experiments. This indicates that hematin was not absorbed to a significant degree and indicate that there is a component of degraded hematin, herein defined as HDA, which is bioavailable when administered orally and produces an anticoagulant effect.

UTILITY SECTION

The HDA of this invention is useful as an orally active anticoagulant by administration of an anticoagulantly effective dose to a patient in need of such treatment. These include, for example, cardiovascular patients, post operative patients or others in need of prevention or treatment of deep venous thrombosis or pulmonary emboluses.

The dosage schedule is of the same order of magnitude as with other therapeutic agents having similar activity. As in standard with anticoagulants, the dosage is individualized for each patient. It will depend upon factors such as age, weight, general physical condition of the patient and other considerations readily evaluated by the physician in attendance. For example, the initial dose may be relatively high, e.g., about 100 mg four times a day for an average adult. Maintenance dosages will be somewhat lower, e.g. 25 mg four times a day. However, as will be known to those skilled in the art, variations from these dosages are possible without loss of useful activity.

The preferred route of administration is oral, but other routes either parenteral or non-parenteral may be employed in special circumstances, as when the patient is unable to cooperate or there is an intransigent blockage of the gastrointestinal tract.

In all methods of administration, the HDA may be used alone or in association with selected pharmaceutical carriers in the form of pharmaceutical compositions containing effective amounts of the active agent. The compositions may be prepared for relatively rapid absorption or in sustained release forms.

For buccal and sublingual administration the active ingredient can be formulated in tablet form with water soluble binding agents such as certain types of clay, starch, lactose or other palatable carbohydrates.

For rectal administration, suppositories or inserts containing the active ingredient dispersed in such reagents as cocoa butter, petroleum, or other natural lubricant, or in a synthetic emmolient such as polyethylene glycol 1000 or polyethylene glycol 4000 are useful.

Transdermal administration will normally be from a sustained release preparation which may be applied as a patch or a gauze applied to the skin.

One convenient procedure for sustained release is to formulate the anticoagulant in a time disintegrating tablet or pellet coated with various thicknesses of known materials such as carnauba wax, cellulose esters and ethers, fats, keratin, gluten or various natural or synthetic esters. Tablets in which the active agent is contained in a slowly dissolving core such as a core of stearic acid or castor oil are useful. Mixed release granule tablets comprising mixtures of the drug itself and the drug in separate particles coated with materials which dissolve at different rates such as dehydrogenated castor oil or fatty acids can also be employed.

What is claimed is:

1. An orally active anticoagulant isolated from hematin and characterized by the following properties:
   a. activity is inhibited by freshly prepared hematin,
   b. activity is inhibited by tin protoporphyrin IX,
   c. activity is inhibited by imidazole,
   d. activity is inhibited by desferrioxamine,
   e. the inhibition by imidazole is reversed by ferric citrate,
   f. activity is stable in the presence of ferrioxamine,
   g. activity is stable in the presence of protoporphyrin IX, and
   h. active in presence of iron.

2. A pharmaceutical composition comprising a pharmaceutically acceptable carrier and an orally active anticoagulant isolated from hematin and characterized by the following properties:
  a. activity is inhibited by freshly prepared hematin,
  b. activity is inhibited by tin protoporphyrin IX,
  c. activity is inhibited by imidazole,
  d. activity is inhibited by desferrioxamine,
  e. the inhibition by imidazole is reversed by ferric citrate,
  f. activity is stable in the presence of ferrioxamine,
  g. activity is stable in the presence of protoporphyrin IX, and
  h. active in presence of iron.

3. A pharamceutical composition as in claim 2 in a form for parenteral administration.

4. A pharamceutical composition as in claim 2 in a form for oral administration.

5. A method of treating a patient in need of treatment with an anticoagulant which comprises administering to the patient an anticoagulantly effective amount of an orally active anticoagulant isolated from hematin and characterized by the following properties:
  a. activity is inhibited by freshly prepared hematin,
  b. activity is inhbited by tin protoporphyrin IX,
  c. activity is inhibited by imidazole,
  d. activity is inhibited by desferrioxamine,
  e. the inhibition by imidazole is reversed by ferric citrate,
  f. activity is stable in the presence of ferrioxamine,
  g. activity is stable in the presence of protoporphyrin IX, and
  h. active in presence of iron.

6. A method as in claim 5 wherein the anticoagulant is administered orally.

7. A method as in claim 5 wherein the anticoagulant is administered parenterally.

* * * * *